United States Patent [19]

Fudenberg et al.

[11] Patent Number: 4,564,517

[45] Date of Patent: Jan. 14, 1986

[54] METHOD FOR EVALUATING PARAMETERS RELATED TO THE THERAPEUTIC AND/OR PROPHYLACTIC TREATMENT OF SOLID NEOPLASMS IN HUMANS

[76] Inventors: Herman H. Fudenberg, P.O. Box 118, Isle of Palms, S.C. 29451; Kwong Y. Tsang, P.O. Box 264, Mount Pleasant, S.C. 29464

[21] Appl. No.: 582,452

[22] Filed: Feb. 22, 1984

[51] Int. Cl.[4] .......................... A61K 49/00; C01N 33/48

[52] U.S. Cl. .......................... 424/9

[58] Field of Search .......................... 424/9

[56] References Cited

U.S. PATENT DOCUMENTS 4,361,544 11/1982 Goldenberg .......................... 424/9

OTHER PUBLICATIONS

Cortes, E. P. et al., "Amputation and Adriamycin in Primary Osteosarcoma. A Five Year Report", Cancer Treat. Re., 62, 271–277 (1978).

Jaffe, N. et al., "High-Dose Methotrexate in Osteogenic Sarcoma. A Five Year Experience", Cancer Treat. Rep., 62, 259–264 (1978).

Sutow, W. W. et al., "Multi-Drug Chemotherapy in Primary Treatment of Osteosarcoma, J. Bone Joint Surg., 58A, 629–633 (1976).

Levin, A. S. et al., "Osteogenic Sarcoma: Immunologic Parameters Before and During Immunotherapy with Tumor-Specific Transfer Factor", J. Clin. Invest., 55, 487–499 (1975).

Byers, V. S., et al., "Immunotherapy of Osteogenic Sarcoma with Transfer Factor. Long Term Follow Up", Cancer Immunol. Immunother., 6, 243–253 (1979).

Singh, I. et al., "A Model for Human Osteosarcoma in Hamsters", Clin. Orthop. Rel. Res., 144, 305–310 (1979).

Tsang, K. Y. and Fudenberg, H. H., "Isoprinosine as an Immunopotentiator in an Animal Model of Human Osteosarcoma", Int. J. Immunopharmac., 3, 383–389 (1981).

Singh, I. et al., "Isolation and Partial Purification of Plasma Membrane Associated Antigens from Human Osteosarcoma (TE-85) Cells in Tissue Culture", Cancer Res., 36, 4130–4136 (1976).

Burger, D. R. et al., "Assessment of Reactivity to Tumor Extracts by Leukocyte Adherence Inhibition and Dermal Testing", J. Natl. Cancer Inst., 59, 317–324 (1977).

*Primary Examiner*—Sam Rosen

*Attorney, Agent, or Firm*—St. Onge, Steward, Johnston & Reens

[57] ABSTRACT

Non-human animal subjects are inoculated in utero with a preparation consisting essentially of plasma membrane derived from human neoplasma cells and, after birth, further inoculated with a preparation comprising human neoplasma cells. In this manner, the animal subjects are induced to bear a solid tumor which biologically closely simulates the solid tumor in humans, and thus serve as models for evaluating the therapeutic and/or prophylactic effect on solid tumors in humans of various surgical procedures, immunomodulators, chemotherapeutic agents and the like. In particular, the process of the invention can be applied to study of human solid neoplasms such as osteosarcoma, fibrosarcoma, pancreatic adenosarcoma and the like.

13 Claims, No Drawings

METHOD FOR EVALUATING PARAMETERS RELATED TO THE THERAPEUTIC AND/OR PROPHYLACTIC TREATMENT OF SOLID NEOPLASMS IN HUMANS

BACKGROUND OF THE INVENTION

The present invention relates to the fields of therapy and prophylaxis and, more particularly, to methods for evaluating various parameters related to the therapeutic and/or prophylactic treatment of solid neoplasms (tumors), such as osteosarcoma, in humans.

Osteosarcoma is a malignancy which occurs primarily during the second decade of life in humans. Although at present there is no known mode of successful long-term therapy for osteosarcoma, various investigators have proposed forms of adjuvant chemotherapy for delaying the occurrence of histologically evident metastases and clinical relapse. See: Cortes, E. P., et al. "Amputation And Adriamycin In Primary Osteosarcoma. A Five Year Report", Cancer Treat. Rep., 62, 271–277 (1978); Jaffe, N., et al., "High-Dose Methotrexate In Osteogenic Sarcoma. A Five Year Experience", Cancer Treat. Rep., 62, 259–264 (1978); Sutow, W. W., et al., "Multi-Drug Chemotherapy In Pulmonary Treatment Of Osteosarcoma", J. Bone Joint Surg., 58A, 629–633 (1976).

Among the more promising potential avenues for treatment of osteosarcoma in humans is the use of osteosarcoma-specific dialyzable leukocyte extract (DLE). In studies conducted by us and others in our group, the immunoprophylactic potency of osteosarcoma-specific DLE against lung metastases in humans was shown to be quite promising, as five of six patients without previous overt tumor who received the osteosarcoma-specific DLE for twenty-four months survived for at least five years. Levin, A. S., Byers, V. S., Fudenberg, H. H., Wybran, J., Hackett, A. J., Johnston, J. O., and Spitler, L. E., "Osteogenic Sarcoma: Immunologic Parameters Before And During Immunotherapy With Tumor-Specific Transfer Factor", J. Clin. Invest., 55, 487–499 (1975); Byers, V. S., LeCam, L., Levin, A. S., Johnston, J. O., and Hackett, A. J., "Immunotherapy Of Osteogenic Sarcoma With Transfer Factor. Long Term Follow Up", Cancer Immunol. Immunother., 6, 243–253 (1979).

Among the most difficult problems in seeking effective therapeutic and prophylactic treatment of any disease or condition in humans is the need for a means of evaluating a particular drug or treatment regimen without having to resort to experimentation with human subjects themselves. Obviously, concerns are ever-present with respect to the use of human subjects as hosts in which to evaluate potential treatments having unknown or poorly understood direct effects and/or side effects. Moreover, as is often the case, even treatments which are known to be safe and effective for humans in general desirably should be patterned to the particular subject in question, either in terms of required dosages, administration regimens, required adjuvants, and other like considerations.

As a consequence of this time-honored and obvious limitation on evaluating parameters related to treatment of human subjects, investigators have long resorted to, and continue to search for, means for providing objective indices of effectiveness and consequences of particular treatments in humans. Numerous techniques are known for use of in vitro assays (utilizing either the cells or fluids of a human subject or of an animal subject) or in vivo studies using animal subjects as predictors of effects in human subjects of various treatments, establishing proper dosages for use in humans and the like. However, in many cases the degree to which either in vivo animal studies or in vitro assays accurately mimic conditions encountered in human subjects is limited and, hence, such techniques cannot be relied upon as indicators of human subject response to particular treatments.

In the field of osteosarcoma therapy and prophylaxis, animal models have been proposed for study of the potential effect of a variety of immunomodulators and/or chemotherapeutic agents on human subjects. See, for example, Singh, I., Tsang, K. Y. and Blakemore, W. S., "A Model for Human Osteosarcoma In Hamsters", Clin. Orthop. Rel. Res., 144, 305–310 (1979); Tsang, K. Y. and Fudenberg, H. H., "Isoprinosine As An Immunopotentiator In An Animal Model Of Human Osteosarcoma", Int. J. Immunopharmac., 3, 383–389 (1981). Although to certain degrees successful as predictors of human response to particular treatments, further improvement in these models is required in order to attain higher degrees of accuracy in predicting human responses and developing other information needed in evaluating potential therapeutic and prophylactic treatments. In particular, improvement is required in providing animal models not only for osteosarcoma tumors, but also with respect to all solid neoplasms in humans.

In accordance with the present invention, an animal model is described which behaves biologically in a manner closely similar, if not identical, to that of humans with solid neoplasms such as osteosarcoma, fibrosarcoma, pancreatic adenosarcoma, and the like, and hence provides a means for evaluating parameters related to use of therapeutic and/or prophylactic agents and treatments in humans.

SUMMARY OF THE INVENTION

In the method of the present invention, a human neoplasma is induced in non-human animal subjects, such as inbred hamsters, by first selectively tolerizing the hamsters in utero with a preparation consisting essentially of plasma membrane isolated from the appropriate human neoplasma cells, followed by introduction into the non-human subject, after birth, of human neoplasma cells per se. The tumors which develop according to this method exhibit high antigenicity. Thereafter, any number of potential therapeutic or prophylactic treatments can be investigated using these animals and suitable control animals.

Comparison of results obtained using animals treated according to the foregoing method with results which have been obtained over long periods of study with human subjects (for example, treatment of human osteosarcoma with dialyzable leukocyte extract) show that the animal model is a highly accurate indicator of the course of solid tumors in humans and the effectiveness of treatments therefor. In the following, the foregoing is illustrated with respect to particular examples.

A key feature of the present invention is the in utero tolerization of the particular non-human subject utilizing plasma membrane isolated from the appropriate human neoplasma cells. In previous work, described in the earlier referred to articles by Singh. et al. (Clin. Orthop. Rel. Res., 144, 305–310 (1979)) and Tsang and Fudenberg (Int. J. Immunopharmac., 3, 383–389

(1981)), animal models of a particular human neoplasm (osteosarcoma) relied upon in utero tolerization utilizing a homogenate of human osteosarcoma cells cultured in a medium containing 10% fetal bovine serum. This homogenate contains both cytoplasmic and membrane proteins from the human osteosarcoma cells, as well as fetal bovine serum proteins which can be incorporated onto cell membranes during culturing. As earlier noted, this previous work was to a certain degree successful in generating a model of a human osteosarcoma tumor in a non-human subject. In the method of the present invention, however, the solid tumors induced are significantly more antigenic and tumorigenic and serve as more accurate models of human tumors. In the present invention, therefore, the in utero tolerization is conducted using a preparation consisting essentially of plasma membrane isolated from the appropriate human neoplasm cells, i.e., a preparation substantially (preferably, completely) free of cytoplasmic proteins or other components (e.g., fetal bovine serum proteins) which would deleteriously affect the high degree of antigenicity and tumorigenicity attained through use of plasma membrane isolated from the human neoplasm cells.

DETAILED DESCRIPTION OF THE INVENTION

The present invention is applicable to any solid neoplasm (tumor) in humans, as well as to use of a variety of animals to induce therein growth of the human tumor. The key steps of the process include in utero selective tolerization of the animal with the plasma membrane isolated from cells obtained from a solid human tumor and, after birth of the tolerized animal, inoculation with cells obtained from a solid human tumor. After the human tumor has grown in the animal to a suitable size, any number of treatments can thereafter be investigated.

Our most detailed investigations have involved the preparation of animal models bearing human osteosarcoma tumor, and the detailed examples which follow demonstrate the invention as applied to this tumor. However, the invention is broadly applicable to any solid neoplasm in humans (for example, fibrosarcoma, pancreatic adenosarcoma), following the techniques discussed in detail herein regarding human osteosarcoma. Accordingly, the examples presented are intended to be illustrative of the invention, and are not to be understood as a limitation of its scope.

In the first example presented, the effectiveness of dialyzable leukocyte extract (DLE) on human osteosarcoma is investigated using a hamster model.

EXAMPLE I

In the first step of the process, plasma membrane is isolated from an osteosarcoma human cell line. Approximately $1\times10^8$ TE-85 cells were washed and ruptured in a Dounce homogenizer. Following rupture and centrifugation at 4000 xg for 10 minutes at 4° C., the supernatant was decanted and saved. A discontinuous sucrose gradient was made with the supernatant by equilibration with 45% sucrose (volume). 13.5 ml of equilibrated 45% sucrose were placed in a cellulose nitrate centrifuge tube (38.7 ml). Then 8.6 ml of 35% sucrose were carefully layered over this, followed by 8.6 ml of 30% sucrose, over which was layered 6 ml of 25% sucrose. Finally, 2 ml of 0.05M Tris buffer (pH 7.4) were added. The discontinuous gradient was then centrifuged in a Beckman L3-50 ultracentrifuge at 23,000 rpm (70,000 xg) for sixteen hours at 4° C. The membrane pellet was resuspended in 0.05M Tris-HCl (pH 7.4) and ultracentrifuged at 23,000 rpm for one hour. The pellet was then resuspended in a discontinuous sucrose gradient, as above described, and centrifuged for 16 hours at 4° C. and 23,000 rpm. The plasma membrane fraction was then recovered from the bottom of the tube. See Singh, I., Tsang, K. Y. and Blakemore, W. S., "Isolation And Partial Purification Of Plasma Membrane Associated Antigens From Human Osteosarcoma (TE-85) Cells in Tissue Culture", Cancer Res., 36, 4130–4136 (1976), incorporated herein by reference.

For induction of the human osteosarcoma, laparotomies were performed on pregnant inbred LSH/SsLAK hamsters (12–14 days gestation). The uterus was exposed and the fetuses (6–10 per hamster) identified. Plasma membrane isolated from TE-85 cells (as above described) in 0.1 ml of medium RPMI-1640 containing 500 μg of the plasma membrane proteins was injected into each fetus through the intact uterine wall. After birth, $2\times10^6$ TE-85-M-MSV cells (TE-85 cells infected with MSV-RD-114 pseudo type virus), suspended in 0.25 ml of medium RPMI-1640, were injected adjacent to the midshaft of the femur of 4 day-old hamsters (previously injected in utero as described above). Tumors developed in 100% of the hamsters.

The hamsters treated according to the method set forth were then used in evaluation of DLE in treatment and prophylaxis.

Three types of DLE were prepared from peripheral blood leukocytes by the general method of Levin et al. (J. Clin. Invest., 55, 487–499, supra, describing DLE preparation from humans): (a) OS specific DLE (DLE-OSAA) was prepared from rabbits immunized with osteosarcoma associated plasma antigens (OSAA). 500 μg of OSAA obtained from TE-85 cells were used for immunization of rabbit. OSAA was injected intradermally into all four extremeties of a female New Zealand white rabbit (9–10 lbs.) at weekly intervals for 3 consecutive weeks; (b) DLE prepared from PPD immunized rabbits (DLE-PPD). For PPD injection, 200 mg of PPD were used for the 1st and 2nd week. 2 ml of complete Freund's adjuvant was used for the 3rd week; (c) DLE prepared from fibrosarcoma antigen extract (FSA) immunized rabbits (DLE-FSA); and (d) DLE prepared from 0.85% NaCl injected rabbits (DLE-NaCl). Three weeks after antigen injections, skin testing was performed on the immunized rabbits. Only those rabbits that showed strong positive skin tests were used as donors for DLE preparations. The specificity of each DLE preparation was assayed by leukocyte adherence inhibition and skin test against various antigen preparations.

Beginning at day one after amputation, DLE was administered subcutaneously into osteosarcoma-bearing hamsters twice per week for the first 6 months and then twice monthly, each injection contained DLE derived from $10^7$ rabbit leukocytes.

For each experiment, tumor-bearing hamsters were amputated when the tumor was palpable in order to remove the tumor mass. The animals were divided into 5 groups of 20 animals each. Group 1 was treated by amputation alone; group 2, by amputation plus DLE-OSAA; group 3, by amputation plus DLE-PPD; group 4, by amputation plus DLE-NaCl; and group 5, by amputation plus DLE-FSA.

In vitro cell-mediated immunity of the DLE treated hamsters was evaluated by both leukocyte adherence inhibition (LAI) (Burger, D. R., et al., "Assessment Of Reactivity To Tumor Extracts By Leukocyte Adherence Inhibition And Dermal Testing", J. Natl. Cancer Inst., 59, 317–324 (1977)), and lymphocyte DNA synthesis (LDS) assays (Adkinson, N. F., et al., "Early Detection Of Lymphocyte Stimulation And Mixed Lymphocyte Interaction In Man With A Semimicro Protein Synthesis Assay", J. Immunol., 112, 1426 (1974)). For the LDS assay, lymphocytes were used at $0.5\times10^5$ cells/well. 1 uCi of [$^3$H]-leucine was added to each culture. OSAA was used in a concentration of 20 $\mu$g/well. KCl extracts of CAMA-1 cell (breast cancer cell line) were used as control. After 4 hours the cultures were harvested. The results, expressed as stimulation index (SI), were obtained by dividing the average counts per minute with antigen by the average count per minute of control culture without antigen. Ear swelling assays at 24 hours were also used as a measure of delayed cutaneous hypersensitivity.

Tumors in the treated hamsters became palpable 10–15 days following cell inoculation. The longest survival was 49 days after tumor development and the mean survival time was 36 days. Light microscopy study of the induced tumors indicated that they were invasive and destructive of the host bone and muscle tissue. New bone and osteoid were present in variable amounts. Light microscopy of the pulmonary tissue showed an extremely cellular field containing pleomorphic cells with hyperchromatic nuclei. The malignant cells were invading and replacing normal pulmonary tissue. Examination of 92 cells from the induced tumor in the third passage in tissue culture indicated that the cells had the chromosomal characteristics and the marker chromosome of the cultured TE-85 cells.

TABLE 1

| Effects of various preparations of DLE on tumor metastasis | | | | | | | | | | | | |
|---|---|---|---|---|---|---|---|---|---|---|---|---|
| | Month after amputation | | | | | | | | | | | |
| Treatment | 0.5 | 1 | 2 | 3 | 4 | 5 | 6 | 7 | 8 | 9 | 10 | 11 |
| NO DLE | 0/20 (0) | 14/20 (70) | 20/20 (100) | | | | | | | | | |
| DLE-OSSA | 0/20 (0) | 0/20 (0) | 3/20 (15) | 4/20 (20) | 4/20 (20) | 6/20 (30) | 11/20 (55) | 12/20 (60) | 12/20 (60) | 12/20 (60) | 13/20 (60) | 13/20 (65) |
| DLE-PPD | 0/20 (0) | 12/20 (60) | 20/20 (100) | | | | | | | | | |
| DLE-NACL | 0/20 (0) | 10/20 (50) | 20/20 (100) | | | | | | | | | |
| DLE-FSA | 0/20 (0) | 12/20 (60) | 20/20 (100) | | | | | | | | | |

20 Animals were used in each treatment group.

Results are expressed in $\frac{\text{number of animals developing metastases}}{\text{total number of animals}}$ Parentheses = % of animals which developed metastases Table 1 shows the incidence of the pulmonary metastases in amputated osteosarcoma-bearing hamsters after treatment with different types of DLE. No metastasis was seen in any of the groups at 0.5 months after amputation. All the animals in the control groups developed pulmonary metastases within 2 months post amputation. In contrast, only 3 of the 20 animals in group 2 developed metastases within 2 months post amputation. (At 11 months post amputation, of the 20 animals in this group, 13 had pulmonary metastases).

As to the survival rates of osteosarcoma-hamsters receiving treatment with various types of DLE, 60% of the DLE-OSAA treated animals were still alive at 330 days post amputation. All animals in groups 1, 3, 4 and 5 died within 1–3 months post amputation.

In a separate experiment, results were obtained for the LAI reactivity on the animals treated with various types of DLE at 0.5 month and 1 month post amputation. Adherence inhibition of less than 20% was not significantly different from controls as previously determined in our laboratory. Animals in groups 1, 3, 4 and 5 had low LAI reactivities at 0.5 month and 1 month post amputation. Only 20% of the animals in group 2 had decreased LAI reactivity at 1 month post amputation. The results of LAI reactivity at 0.5 month post amputation when a KCl extract of CAMA-1 cells was used as the antigen source indicated that the LAI reactivity was at the control level in all 5 groups. The results of the lymphocyte DNA synthesis activity at 0.5 month and 1 month post amputation showed that the SI in groups 1, 3, 4 and 5 animals were low when determined at 0.5 month and 1 month post amputation. Only 20% of the animals in group 2 had decreased LDS at 1 month post amputation. When a KCl extract of CAMA-1 cells was used as the antigen source, the results of LDS activity was at the control level in all animals. Tables 2 and 3 show the results of LAI reactivity and LDS activity of the surviving animals in group 2 at 4 and 8 months post amputation. Both LAI reactivity and LDS were significantly higher ($p<0.001$) with OSAA as antigen than with KCl extracts of CAMA-1 cells as the antigen source.

TABLE 2

Effect of DLE-OSAA on the cell-mediated immunity of the surviving animal at 4 months post amputation.

| Animal number | LAI[a] OSAA | LAI[a] OAMA-1 | SI[b] OSAA | SI[b] OAMA-1 |
|---|---|---|---|---|
| 1 | 50.1 ± 8.6* | 15.1 ± 2.3 | 7.23 ± 0.4* | 1.09 ± 0.2 |
| 2 | 44.2 ± 7.5* | 10.2 ± 1.4 | 5.06 ± 0.8* | 0.92 ± 0.1 |
| 3 | 40.1 ± 6.3* | 10.4 ± 1.0 | 4.01 ± 0.3* | 1.03 ± 0.09 |
| 4 | 41.4 ± 7.2* | 11.4 ± 1.2 | 6.14 ± 0.2* | 0.98 ± 0.07 |
| 5 | 53.4 ± 9.1* | 12.9 ± 0.8 | 7.62 ± 1.6* | 0.89 ± 0.1 |
| 6 | 46.2 ± 7.3* | 10.5 ± 1.7 | 4.31 ± 1.8* | 1.06 ± 0.3 |
| 7 | 37.4 ± 6.1* | 16.4 ± 0.6 | 4.02 ± 0.9* | 0.97 ± 0.2 |

20 $\mu$g of antigens were used in both assays.

*Significant, $p<0.001$ as determined by Student's t test.

OSAA = osteosarcoma associated antigens

CAMA-1 = KCl extracts of CAMA-1 cells

[a]Results are expressed in % of Leukocyte adherence inhibition.

[b]SI = stimulation index $\left(\frac{\text{cpm with antigen}}{\text{cpm without antigen}}\right)$

TABLE 3

| Animal number | Effect of DLE-OSAA on the cell-mediated immunity of the surviving animals at 18 months post amputation | | | |
|---|---|---|---|---|
| | LAI[a] | | SI[b,c] | |
| | OSAA | OAMA-1 | OSAA | OAMA-1 |
| 1 | 44.2 ± 4.85* | 11.4 ± 0.8 | 5.10 ± 0.3* | 0.96 ± 0.2 |
| 2 | 40.0 ± 6.59* | 9.2 ± 0.4 | 4.4 ± 0.5* | 0.81 ± 0.1 |
| 3 | ND | ND | ND | 0.85 ± 0.1 |
| 4 | 35.1 ± 5.56* | 8.4 ± 0.3 | 2.8 ± 0.3* | 1.05 ± 0.2 |
| 5 | 32.4 ± 3.03* | 11.6 ± 0.8 | 4.7 ± 0.4* | 0.82 ± 0.4 |
| 6 | 34.5 ± 5.54* | 10.9 ± 0.7 | 3.2 ± 0.2* | 0.94 ± 0.2 |
| 7 | 42.4 ± 8.37* | 12.4 ± 1.0 | 2.6 ± 0.4* | 1.02 ± 0.6 |

[a]Results are expressed in % of leukocyte adherence inhibition.

[b]SI = stimulation index $\left(\frac{\text{cpm with antigen}}{\text{cpm without antigen}}\right)$

[c]20 μg of antigens were used in both assays.

*Significant, p<0.01 as determined by Student's t test.

OSAA = osteosarcoma associated antigens

OAMA-1 = KCl extracts of OAMA-1 cells

ND = not done

As is apparent from the foregoing, we attempted in this investigation to extend the lifespan of hamsters by amputation (removal) of the primary tumor mass. We used OS-specific DLE for prophylaxis against pulmonary metastases, the cause of rapid death in such animals bearing human osteosarcoma. The survival rate in the DLE-OSAA group in a 380 day period was much higher (60%) in the DLE-OSAA treated group as compared to the control groups—amputation alone, DLE-PPD treated, DLE-FSA treated and DLE-NaCl treated (all at 0%). The rate of pulmonary metastases in a 380 day period is lower in the DLE-OSAA treated group (66%) as compared to the control groups (100%).

Our group previously reported (see Levin, A. S., et al. and Byers, V. W., et al., supra) the clinical and immunological parameters in osteosarcoma patients given DLE. Of 7 patients with primary tumors not removed at the beginning of OS specific DLE therapy, there was no increase in survival time as compared with historical controls. However, 5 of the 6 patients following tumor resection apparently free of overt metastases at the initiation of OS-specific DLE therapy were alive and disease free at last follow-up 24-32 months after surgery. Compared with the probabilities of 5 years survival computed from historical controls, this is highly significant (p<0.008). This increase in survival time due to prevention of pulmonary metastases in patients treated with OS specific DLE is in concordance with the animal model. In this study the cell mediated immunity as measured by LAI and LDS were strikingly low in animal and control groups at 0.5 month post amputation. [This phenomenon may be due to the removal of the antigen (primary tumor) from the host; decrease of tumor specific CMI in the host after tumor removal has been reported by other investigators.] Both LAI and LDS activity in experimental animals were high when measured at 0.5 month, 11 month, 14 months and 18 months, suggesting that administration of DLE-OSAA increased OS specific CMI. Three of the animals in group 3 and 2 of the animals in group 4 had increased LAI and LDS activity when measured at 1 month. This result may be due to the presence of micrometastases but not to widespread metastases in the host. The low LAI and LDS activity in most of the animals in the control groups at 1 month presumably is due to the presence of tumor metastases in these animals. These results are similar to findings that CMI of osteosarcoma patients increased dramatically after injection of OS-tumor specific DLE. The results obtained in this investigation indicate that OS-hamsters given DLE-OSAA after amputation have a far better survival rate than corresponding animals treated by (a) amputation alone, or (b) DLE-PPD lacking OS specific transfer factor, or (c) DLE-NaCl or DLE-FSA (fibrosarcoma is closely related immunologically to osteosarcoma). The evidence of the capability of DLE-OSAA to enhance specific CMI against OS is reflected by the increases in LAI and LDS activity.

The animal model described in this Example is unique, and the DLE-OSAA is specific and can be used for further investigation of the other effects of osteosarcoma specific DLE alone and in combination with other immunomodulating and chemotherapeutic agents in the therapy of human osteosarcoma. The information obtained from these studies is relevant to the treatment of osteosarcoma in humans. In addition, this animal model can be used in the evaluation of the effectiveness of various immune potentiating drugs, and can be individualized to a given point.

EXAMPLE II

In this example, the animal model of human osteosarcoma described in Example I is utilized to investigate the immunomodulating effect of MAHQ, a 2-amino-4-hydroxyquinazoline which inhibits the enzyme thymidylate synthase and appears to inactivate suppressor (rather than helper) T cells.

The investigation was conducted as follows:

Determination of maximum tolerated dose of MAHQ in hamsters. 4-month-old inbred hamsters were injected intraperitoneally with various concentrations of MAHQ (20, 50, 80, 120, 150 and 200 mg/kg), and the survival rate was determined 1 week post injection.

Lymphocyte proliferation assays. Phytohemagglutinin (PHA) and *Escherichia coli* lipopolysaccharide (LPS) were used as mitogens for lymphocytes from 3-month-old normal inbred hamsters. In this method, $10^6$ lymphocytes were cultured for 72 hours in the presence of 40 μg PHA or 20 μg LPS per ml. Lymphocyte cultures that did not receive any mitogens served as unstimulated controls. The cells were pulsed with 1 μCi of [$^3$H]-thymidine (2.0-6.0 Ci/mmol, Amersham-Searle) for the final 12 hours of incubation. At the end of the labeling time, the cells were harvested with a Mash II cell harvester. The radioactivity was counted in a Packard scintillation counter.

Natural killer cell (NK) cytotoxicity assay. $^{51}$Cr-labelled Raji cells were used as target cells for hamster NK cells in a cytotoxicity assay. Ratios (effector:target) of 100:1 and 50:1 were used in this assay. Target cells incubated without effector cells were used to determine the level of spontaneous lysis. The plates were incubated for 4 hours at 37° C. in a 5% $CO_2$ incubator. Maximum lysis was determined by addition of 10% Triton X-100 solution (no effector cells) instead of medium to the wells. The cytotoxicity was calculated as follows:

$$\%\ \text{lysis} = \frac{\text{mean cpm test lysis} - \text{mean cpm spontaneous lysis}}{\text{mean cpm maximum lysis} - \text{mean cpm spontaneous lysis}} \times 100$$

Determination of the effect of IAHQ on tumor development. IAHQ in distilled water was injected intraperitoneally (50 mg/kg/injection) at the same time that TE-85-M-MSV cells were injected adjacent to the midshaft of the femur into 4-day-old hamster (see procedure in Example I). A second injection of IAHQ (50 mg/kg) was given on day 10 after the first injection. No IAHQ was injected in the control group (saline controls). The animals were examined daily for tumor development.

Effects of IAHQ on the survival rate of hamsters. Various concentrations of IAHQ were injected intraperitoneally into 1-month-old hamsters (20 per group), and the survival rates were determined 1 week later. The maximum tolerated dose for the hamsters tested was 50 mg/kg. When 120 mg/kg IAHQ was used, 60% of the hamsters were dead 1 week postinjection. At 150 mg/kg, only 10% of the hamsters survived. All the hamsters died when 200 mg/kg was used.

Effects of IAHQ on mitogen stimulation. PHA-induced lymphocyte proliferation was inhibited more than 80% 1 day after intraperitoneal injection of 80 mg/kg IAHQ and returned to normal by day 12. Similar results were obtained for LPS-induced lymphocyte proliferation, which was inhibited more than 90% on the second day postinjection and returned to normal by day 12.

Effects of IAHQ on NK cytotoxicity. The effects of IAHQ on NK cytotoxicity assays were similar to those on mitogen-induced lymphocyte proliferation. When 3-month-old hamsters were injected intraperitoneally with IAHQ (50 mg/kg), the mean % lysis decreased to approximately 10% on day 2 postinjection and returned to normal (about 50%) by day 12.

Effects of IAHQ on tumor development. In the control group (without IAHQ), 100% (40/40) of the hamsters developed osteosarcoma by day 20 postimplantation of TE-85-M-MSV cells. Pulmonary metastases were detected 15–20 days after the development of the tumor. In the experimental group, only 32% (13/40) developed osteosarcoma by 21 days postimplantation, and two more developed osteosarcoma by 25 days. No pulmonary metastases were detected in any of these IAHQ-treated tumor-bearing hamsters. The remaining IAHQ-treated animals were tumor-free 3 months postinjection.

In the foregoing Examples of the present invention, therefore, an accurate model of human osteosarcoma is developed in a non-human subject which behaves in a manner biologically similar, if not identical, to osteosarcoma in a human host. According to the invention, a non-human subject, particularly a hamster, is tolerized in utero with a preparation consisting essentially of purified plasma membrane from a human osteosarcoma cell line and then inoculated, after birth, with a preparation comprising human osteosarcoma cells. In conjunction with development of the osteosarcoma tumor in the non-human subject, a variety of surgical treatments, therapeutic agents and the like can be evaluated.

A particular advantage of the present invention is the ability to individualize treatment for a particular patient. Thus, cells (tissue) obtained from an osteosarcoma tumor-bearing patient at surgery are used as the human osteosarcoma cells for in utero tolerization and subsequent inoculation in a number of laboratory animals. Different therapies can then be evaluated in these animals to determine which may be particularly suitable for the patient in question, rather than relying on generalized findings from previous experimentation. Even where a particular treatment (e.g., use of osteosarcoma-specific DLE) is readily indicated, laboratory animals in which the model tumor has been grown can then be used to determine optimum DLE parameters such as donors, dosages, administration regimens and the like.

In the generalized practice of the invention for evaluating parameters related to treatment and/or prophylaxis of a given solid tumor in human subjects, a non-human animal subject is inoculated in utero with a preparation consisting essentially of purified plasma membrane derived from cells from the given solid tumor in a human; after birth of the animal, it is inoculated with a preparation comprised of cells again derived from the given solid tumor in a human; and the animal subject then used to evaluate, e.g., therapeutic and/or prophylactic effectiveness of drugs, immunomodulators, etc., as well as parameters such as dosages, administration regimen, and the like.

The particular embodiments of the invention set forth herein are believed to adequately illustrate the essential features of the invention and its applicability to a wide field of human neoplasms. Variations or modifications obviously can be employed by those of skill in the art without departing from the scope and spirit of the invention, as defined by the appended claims.

What is claimed is:

1. A method for evaluating parameters related to treatment and/or prophylaxis of solid tumors in human subjects, comprising:

(a) inoculating a non-human animal subject in utero with a preparation consisting essentially of plasma membrane derived from cells of a given human solid tumor and free of cytoplasmic proteins to induce antigen specific tolerance;

(b) after birth of said non-human animal subject, inoculating said animal with a preparation comprising cells obtained from said given human solid tumor so as to induce in said animal subject said given human solid tumor; and (c) utilizing said animal subject as a host for evaluating the effects of one or more therapeutic and/or prophylactic measures on said given human solid tumor.

2. The method according to claim 1 wherein said non-human animal subject is an inbred hamster.

3. The method according to claim 1 wherein said therapeutic and/or prophylactic measures comprise the administration of immunomodulators to said non-human animal subject.

4. The method according to claim 3 wherein said immunomodulators comprise dialyzable leukocyte extracts specific for said given human solid tumor.

5. The method according to claim 1 wherein said therapeutic and/or prophylactic measures comprise the administration of chemotherapeutic agents to said non-human animal subject.

6. The method according to claim 1 wherein said given human solid tumor is selected from the group consisting of osteosarcoma, fibrosarcoma and pancreatic adenosarcoma.

7. A method for evaluating parameters related to treatment and/or prophylaxis of osteosarcoma tumors in human subjects, comprising (a) inoculating a non-human animal subject in utero with a preparation consisting essentially of plasma membrane derived from human osteosarcoma cells and free of cytoplasmic proteins;

(b) after birth of said non-human animal subject, inoculating said animal with a preparation comprising human osteosarcoma cells so as to induce in said animal subject an osteosarcoma tumor; and (c) utilizing said animal subject as a host for evaluating the effects of one or more therapeutic and/or prophylactic measures on human osteosarcoma tumor.

8. The method according to claim 1 wherein said non-human animal subject is an inbred hamster.

9. The method according to claim 8 wherein said human osteosarcoma cells comprise cell line TE-85.

10. The method according to claim 8 wherein said human osteosarcoma cells comprise cells removed from an osteosarcoma tumor of a human patient in whom it is desired to take particular therapeutic and/or prophylactic measures.

11. The method according to claim 8 wherein said therapeutic and/or prophylactic measures comprise the administration of immunomodulators to said non-human animal subject.

12. The method according to claim 11 wherein said immunomodulators comprise osteosarcoma-specific dialyzable leukocyte extracts.

13. The method according to claim 8 wherein said therapeutic and/or prophylactic measures comprise the administration of chemotherapeutic agents to said non-human animal subject.

* * * * *